United States Patent [19]

Meneghin

[11] Patent Number: 5,191,078
[45] Date of Patent: Mar. 2, 1993

[54] PROCESS FOR THE DIRECT AND REGIOSELECTIVE FUNCTIONALIZATION IN POSITION 2 OF PHENOTHIAZINE

[75] Inventor: Mariano Meneghin, Revine-Lago, Italy

[73] Assignee: Zambon Group S.p.A., Milan, Italy

[21] Appl. No.: 844,434

[22] Filed: Mar. 2, 1992

Related U.S. Application Data

[62] Division of Ser. No. 626,763, Dec. 13, 1990, Pat. No. 5,109,134.

[30] Foreign Application Priority Data

Dec. 21, 1989 [IT] Italy .................. 22769 A/89

[51] Int. Cl.$^5$ .................. C07D 279/20; C07B 45/04
[52] U.S. Cl. .................................................. 544/35
[58] Field of Search .................................... 544/35

[56] References Cited

U.S. PATENT DOCUMENTS

| | | | |
|---|---|---|---|
| 2,888,459 | 5/1959 | Jacob et al. | 260/243 |
| 3,136,762 | 6/1964 | Mayer et al. | 260/243 |
| 4,451,461 | 1/1983 | Dubroeucq et al. | 544/42 |
| 5,089,613 | 2/1992 | Meneghin | 544/35 |

FOREIGN PATENT DOCUMENTS

| | | |
|---|---|---|
| 0070753 | 1/1983 | European Pat. Off. . |
| 768454 | 2/1957 | United Kingdom . |
| 1480553 | 7/1977 | United Kingdom . |

OTHER PUBLICATIONS

Heterocycles, vol. 26, No. 1, 1987, Saraf et al., "Recent Advances in the Synthesis of Phenothiaines", pp. 239–273.
Knoevenagel Berichte, 1909, pp. 3315–3322.
Chemical Abstracts, vol. 77, No. 19661c (1972), Wanzlick, "3-Mercapto- and 3-(alkylthio)phenothiazines" and DE 2,047,078.
Encyclopedia of Chemical Technology 3rd edition, Kirk-Othmer, vol. 11, (1980), p. 287.
"Reductions in Organic Chemistry," 1986, Hudlicky, p. 90.

Primary Examiner—Mark Berch
Attorney, Agent, or Firm—Stevens, Davis, Miller & Mosher

[57] ABSTRACT

A process for the direct and regioselective functionalization of phenothiazine which allows one to introduce an SH group in position 2 is described. The thus-obtained 2-mercapto-phenothiazine is easily transformed into 2-methylthio-phenothiazine, an important intermediate for the preparation of pharmacological active compounds. One of the reaction routes (described in detail in the specification) involves the production of an N-aryl-phenothiazine-2-sulfinic acid [compound (III)] which can be isolated as a salt (e.g., an alkaline salt) by treatment with an aqueous alkaline solution. Thus compound (III-A) is produced.

1 Claim, No Drawings

PROCESS FOR THE DIRECT AND REGIOSELECTIVE FUNCTIONALIZATION IN POSITION 2 OF PHENOTHIAZINE

This is a division of application Ser. No. 07/626,763, filed Dec. 13, 1990 now U.S. Pat. No. 5,109,134.

The present invention relates to a process for the preparation of 2-methylthio-phenothiazine, an intermediate for the preparation of drugs.

2-Methylthio-phenothiazine of formula

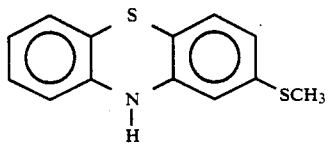

is a known intermediate for the preparation of compounds with pharmaceutical activity among which Thioridazine (Merck Index, XI Ed., No. 9290, page 1474), Mesoridazine (Merck Index, XI Ed., No. 5813, page 929), Methiomeprazine (Merck Index, X Ed., No. 5847, page 857), may be cited.

Compound I is also an intermediate for the synthesis of some of the compounds with contraceptive activity described in U.S. Pat. No. , 4,578,379 and for the synthesis of some of the compounds useful as stabilizers for hydrocarbons described in the Japanese patent application No. 48-28761 [Yoshitomi—(C.A., 81:15387c)].

Several processes for the preparation of compound I are known, among which, for example, the following may be cited: a three-steps synthesis starting from a condensation between 3-methylthionaniline and 2-chloro-benzoic acid which provides compound I with the 4-methylthio isomer as an impurity (Helvetica Chimica Acta, 41, 1063 1958); a four-steps synthesis which requires by first a condensation between sodium 2-bromo-thiophenate and 2-chloro-5-methylthio-nitro-benzene or the condensation between 2-chloro-thiophenol and 2-bromo-5-methylthio-nitrobenzene [Swiss patent No. 404,669, Sandoz—(C.A., 65:15392h)], a synthesis consisting in the condensation between 4-methylthio-thiophenol and 2-chloro-nitrobenzene to obtain 2-nitro-4'-methylthio-diphenylsulfide, its reduction in autoclave at 70 atmospheres, a diazotization and a reduction with decalin of the thus obtained azide [Japanese patent application No. 16283/1962, Yoshitomi—(C.A., 59;11516e)].

British patent No. 863,547 [Sandoz—(C.A., 55:19962d)] describes the preparation of compound I by reacting N-(3-methylthio-phenyl)-aniline with sulfur in the presence of iodine. However, the aniline-derivative must be synthesized separately. Other examples of preparation of phenothiazines are collected in Heterocycles, vol. 26, No. 1, page 239, (1987).

However, the above reported processes show negative features which makes them not very suitable from an industrial point of view. Such negative features include a long synthesis which needs a high number of steps and the separation and purification of the intermediates, starting materials which are not available on the market or available only at high cost, reactants and catalysts of difficult industrial use, low yields or again the formation of by-products of difficult separation.

As far as we know, processes for the preparation of 2-methylthiophenothiazine which use as starting material phenothiazine, a compound available on the market in industrial amounts and at low cost have never been described.

We have now found and it is the object of the present invention a process for the direct functionalization of phenothiazine which allows the regioselective introduction in position 2 of an SH group from which the desired product is obtained by methylation.

Such process comprises the reaction of the phenothiazine N-protected by an acyl group, with sulfur dioxide in the presence of aluminum trichloride to obtain, after work-up of the reaction mixture, phenothiazine-2-sulfinic acid. The reduction of this, in order to obtain 2-mercapto-phenothiazine, and the subsequent S-methylation, allow to prepare 2-methylthio-phenothiazine.

The process object of the present invention uses products and reactants of low cost and of easy industrial use and it provides the desired compound with good yields and with high purity.

The starting product of the process ia an N-acyl-derivative of phenothiazine.

Such derivative can be represented by the following general formula

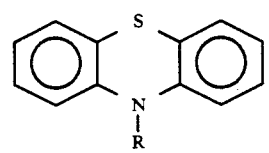

wherein R is an acyl group of a $C_1$–$C_6$ aliphatic carboxylic acid or of benzoic acid and, preferably, it is a formyl, acetyl or benzoyl group.

The compounds of formula II are prepared by acylating phenthiazine with acyl halides or anhydrides or, optionally, also with formic acid according to known techniques.

A great number of the compounds of formula II are already known and, in particular, the preferred compounds are described in the following papers:

N-formyl-phenothiazine [Austral. J. Chem., 8, 252, (1955)]

N-acetyl-phenothiazine (Liebigs Ann., 230, 95)

N-benzoyl-phenothiazine [Berichte, 18, 1843–49, (1885)].

The reaction of compound II with sulfur dioxide ($SO_2$) and aluminum trichloride ($AlCl_3$) carried out without solvent or in an inert solvent, provides the N-acyl-phenothiazine-2-sulfinic acid of formula

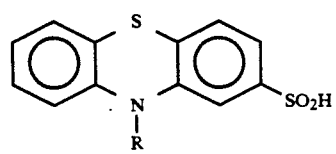

wherein R has the above reported meanings.

The thus obtained compound III is directly reduced in the same reaction environment in order to obtain 2-mercapto-phenothiazine of formula

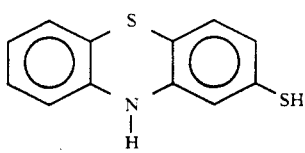

(IV)

Alternatively, compound III can be isolated as a salt, for example an an alkaline salt, by treatment with aqueous alkaline solution.

Such treatment affords the contemporaneous deprotection of the nitrogen in order to obtain a compound of formula

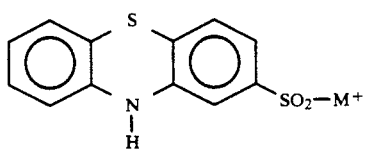

(III-A)

wherein M+ is the cation of an alkali metal, in particular sodium or potassium.

The compounds III-A are new and they are a further object of the present invention.

By reduction, such compounds provide compound IV.

The reduction of compound III as well as of compound III-A is carried out according to conventional techniques suitable to reduce the sulfur atom.

A method, which affords good results with low industrial cost, consists in carrying out the reduction with zinc in acid environment.

Preferably, the thus obtained compound IV is not isolated but directly methylated in the same reaction environment in order to obtain compound I. This reaction is known per se and it is carried out by conventional methylating agents of industrial use such as dimethyl-sulfate.

Clearly, it is possible to alkylate the compound of formula IV with an alkyl different from methyl (for example ethyl), using normal alkylating agents which depend on the nature of the alkyl to be introduced.

Therefore it is possible, for example, to prepare 2-ethylthiophenothiazine, an intermediate useful for the synthesis of a drug known as Thiethylperazine (Merck Index, XI Ed., No. 9241, page 1467).

A practical embodiment of the invention, particularly useful for its industrial application, is the following.

Compound II is treated with aluminum trichloride and sulfur dioxide in order to obtain compound III.

The aluminum trichloride amount should be equimolar with the compound II even if an excess from 2 to 4 times in moles is preferably used.

The reaction is carried out with gaseous $SO_2$. It is preferred first to treat $AlCl_3$ with $SO_2$. A complex is formed to which compound II, as such or dissolved in an inert organic solvent, is added. Alternatively the gaseous $SO_2$ is bubbled into an $AlCl_3$ suspension in an inert solvent.

Examples of suitable solvents are those normally used in the Friedel-Crafts reactions with $AlCl_3$ such as for example $CH_2Cl_2$, $CS_2$, $CHCl_2$—$CHCl_2$, $CH_2Cl$—$CH_2Cl$.

The reaction mixture is kept under $SO_2$ atmosphere and at a temperature between 0° and 100° C., preferably between room temperature and 70° C.

At the end of the reaction, the work-up is carried out by diluting the thus obtained mixture with an inert organic solvent, for example $CH_2Cl_2$.

The reduction step is preferably carried out with zinc and hydrochloric acid and, in practice, it may be carried out directly on the organic solution obtained by dilution of the reaction mixture coming from the sulfinylation step or alternatively after treatment of such solution with acidic water in order to separate the aluminum salts.

The work-up of the reduction mixture with an aqueous alkaline solution and the subsequent acidification afford compound IV which is then methylated according to what above reported.

Alternatively, at the end of the sulfinylation, the compound of formula III-A may be isolated by treatment with an aqueous alkaline solution and it may be subjected to reduction according to the above indicated procedure.

The most typical and innovating aspect of the present process is the sulfinylation step of phenothiazine II which affords compound III or III-A with good yield, with a practically complete regioselectivity of the attack in position 2.

In fact, the presence of products deriving from an attack in position 3 and of products deriving from a disubstitution have not been detected by analytic techniques. In some cases, a low percentage (0.5–0.7%) of the compound deriving from an attack in position 4 was observed, but this compound was completely eliminated in the subsequent steps of the work-up thus providing 2-methylthio-phenothiazine with a purity higher than 99%.

The process object of the invention shows various advantages with respect to the processes of the prior art. Such advantages, whose industrial usefulness is clear to the man of the art, can be summarized in the low cost of the starting-materials, in their easy availability in industrial amounts, in the reduced number of steps (N-acylation of phenothiazine, sulfinylation and reduction in the same reaction environment with contemporaneous deprotection, S-methylation) in the easy industrial application of the above steps, in the high regioselectivity of the process and in the remarkably higher global yield than that obtainable by the known methods.

In order to better illustrate the present invention the following examples are now given.

EXAMPLE 1

Preparation of 2-methylthio-phenthiazine

Into a flask, equipped with mechanical stirrer, thermometer and reflux condenser, anhydrous aluminum trichloride (20 g; 0.15 mol) was charged under nitrogen.

It was kept under stirring in a sulfur dioxide atmosphere, by heating with an oil bath at a temperature of 60° C. for 7 hours.

An oil was obtained to which 10-formyl-phenothiazine (11 g; 0.0484 mol) was added at room temperature and in 20 minutes under slow stirring.

The mixture was kept under stirring in sulfur dioxide atmosphere for 16 hours and then for further 2 hours at 60°–65° C.

After this period, nitrogen was substituted to sulfur dioxide, the reaction mass was left to cool to 30°–40° C.

and methylene chloride (79.53 g) was added in 30 minutes.

The mixture was heated at reflux for further 30 minutes in order to make easy the dissolution of the reaction mass.

The thus obtained solution can undergo two different treatments:

Method A

At room temperature and under stirring, zinc powder (11 g) was added to the solution.

After 10 minutes, hydrochloric acid at 37% (71.16 g) was added in 5 hours and at room temperature. The mixture was kept under stirring at room temperature for 10 hours and then it was heated under reflux for 5 hours. After cooling water (20 g) was added and it was filtered on celite by washing with methylene chloride (5.3 g).

The two phases of the filtrate was separated. The aqueous phase was eliminated. The organic phase (phase a), after a washing with hydrochloric acid at 18.5% (21.8 g), was treated at 0° C. and under nitrogen atmosphere with a cold aqueous sodium hydroxide solution at 5% (84.4 g).

The mixture was stirred for some minutes and then the phases were separated, always at the temperature of 0° C. and under nitrogen.

The aqueous phase, constantly kept at 0° C. and under inert atmosphere, was charged into a flask equipped with mechanical stirrer, thermometer, reflux condenser and external cooling by a bath at −5°/−3° C.

Dimethylsulfate (4.868 g; 0.0386 mol) was added dropwise in 1 hour, under vigorous stirring, while keeping the internal temperature at 0° C.

Hydrochloric acid at 37% (13.046 g) was then slowly added up to a constant pH value of 6.5-7 by keeping the temperature at 0° C.

Toluene was added (69.36 g) and the mixture was heated at reflux for 2 hours. Then, it was warm filtered on celite by washing with warm toluene (8.67 g) and the phases were separated.

The organic phase was washed with water (30 g) at 80° C., concentrated and cooled at 0° C.

2-methylthio-phenothiazine (7.73 g) precipitated having an HPLC titre higher than 99% (65% yield), m.p.=138°-140° C.

Method B

The methylene chloride solution (2.65 g) obtained from the sulfinylation step was added to water (50 g) and hydrochloric acid at 37% (11.86 g), at room temperature and under inert atmosphere. During the addition the internal temperature was kept at −5°/0° C.

The phases were separated. The aqueous phase was eliminated after washing with methylene chloride at 0° C. (18.56 g). Zinc powder (22 g) and, dropwise, hydrochloric acid at 37% (59.30 g) were added to the collected organic phases, kept constantly at 0° C.

At the end of the addition, the mixture was left at 0° C. for 5 hours under stirring, then at room temperature for 10 hours and thereafter at reflux for further 5 hours.

It was then cooled to room temperature and filtered on celite by washing with methylene chloride (5.3 g).

The two phases of the filtrate were separated. The aqueous phase was eliminated. The organic phase was treated exactly as the organic phase of the method A (phase a) obtained after filtration on celite.

EXAMPLE 2

The procedure described in example 1 was repeated in a similar way but by using $AlCl_3$ and 10-formyl-phenothiazine in the molar ratio of 2:1.

2-Methylthio-phenothiazine was obtained in 51% yield and with an HPLC titre higher than 99%.

EXAMPLE 3

The preparation of repeated by working in a way similar to that described in example 1 but by bubbling $SO_2$ into a suspension of $AlCl_3$ in $CS_2$. At the mixture a solution of 10-formyl-phenothiazine in $CS_2$ was added and it is heated at reflux for 3 hours.

At the end $CS_2$ was eliminated, the solution was treated with $CH_2Cl_2$ and the work-up was carried out as described in example 1.

2-Methylthiophenothiazine (40% yield) was obtained with an HPLC titre higher than 99%.

EXAMPLE 4

By working in a way similar to that described in example 3 but by using 1,1,2,2-tetrachloroethane as solvent, 2-methylthiophenothiazine (40% yield) was obtained with an HPLC titre higher than 99%.

EXAMPLE 5

By working in a way similar to that described in example 3 but by using 1,2-dichloroethane as solvent, 2-methylthiophenothiazine (36% yield) was obtained with an HPLC titre higher than 99%.

EXAMPLE 6

By working in a way similar to that described in example 1 but by adding 10-formyl-phenothiazine in 1,1,2-tetrachloroethane to the aluminum trichloride-sulfur dioxide complex.

The solution was kept at 65° C. for 5 hours and then it is worked as described in example 1 thus obtaining 2-methylthiophenothiazine (40% yield) with an HPLC titre higher than 99%.

What we claim is:
1. A compound of formula

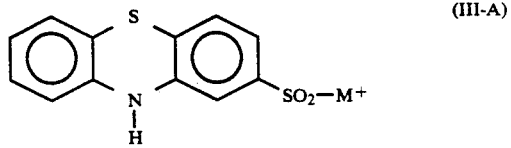
(III-A)

wherein $M^+$ is the cation of an alkali metal.

* * * * *